United States Patent
Do et al.

(10) Patent No.: US 9,629,602 B2
(45) Date of Patent: Apr. 25, 2017

(54) SYSTEM AND METHOD FOR ULTRA-HIGH RESOLUTION TOMOGRAPHIC IMAGING

(71) Applicant: THE GENERAL HOSPITAL CORPORATION, Boston, MA (US)

(72) Inventors: Synho Do, Lexington, MA (US); Thomas Brady, Cambridge, MA (US); Rajiv Gupta, Wayland, MA (US)

(73) Assignee: The General Hospital Corporation, Boston, MA (US)

(*) Notice: Subject to any disclaimer, the term of this patent is extended or adjusted under 35 U.S.C. 154(b) by 29 days.

(21) Appl. No.: 14/758,921

(22) PCT Filed: Jan. 6, 2014

(86) PCT No.: PCT/US2014/010307
§ 371 (c)(1),
(2) Date: Jul. 1, 2015

(87) PCT Pub. No.: WO2014/107651
PCT Pub. Date: Jul. 10, 2014

(65) Prior Publication Data
US 2015/0335306 A1 Nov. 26, 2015

Related U.S. Application Data

(60) Provisional application No. 61/749,151, filed on Jan. 4, 2013.

(51) Int. Cl.
*A61B 6/00* (2006.01)
*A61B 6/03* (2006.01)
(Continued)

(52) U.S. Cl.
CPC .............. *A61B 6/548* (2013.01); *A61B 6/032* (2013.01); *A61B 6/037* (2013.01); *A61B 6/4021* (2013.01);
(Continued)

(58) Field of Classification Search
CPC ........... A61B 6/42; A61B 6/027; A61B 6/032; A61B 6/035; A61B 6/037; A61B 6/4021;
(Continued)

(56) References Cited

U.S. PATENT DOCUMENTS 3,250,916 A * 5/1966 Rogers ................. G02B 27/023
378/134
4,072,875 A * 2/1978 Webley ................... H01J 35/26
313/149

(Continued)

FOREIGN PATENT DOCUMENTS

RU 2246258 C1 2/2005

OTHER PUBLICATIONS

The International Search Report and Written Opinion as mailed on May 7, 2014 for International Application No. PCT/US2014/010307.

*Primary Examiner* — Irakli Kiknadze
(74) *Attorney, Agent, or Firm* — Quarles & Brady LLP

(57) ABSTRACT

A system and method for producing an image of a subject with a tomographic imaging system are provided. A tomographic imaging system is operated to rotate a radiation detector, radiation source, or both through a plurality of angular positions around a subject while acquiring data. As the radiation detector or source is rotated, the radiation detector or source is shifted at each angular position by a different shift value. An image of the subject is reconstructed from the acquired data using a reconstruction technique that incorporates the shifts applied to the detector, source, or both into a system matrix.

19 Claims, 15 Drawing Sheets

(51) Int. Cl.
*G06T 11/00* (2006.01)
*A61B 6/02* (2006.01)

(52) U.S. Cl.
CPC .............. *A61B 6/4085* (2013.01); *A61B 6/42* (2013.01); *A61B 6/4452* (2013.01); *A61B 6/5205* (2013.01); *G06T 11/005* (2013.01); *A61B 6/027* (2013.01); *A61B 6/035* (2013.01); *A61B 6/4028* (2013.01); *A61B 6/482* (2013.01)

(58) Field of Classification Search
CPC ... A61B 6/4028; A61B 6/4085; A61B 6/4452; A61B 6/482; A61B 6/5205; A61B 6/548; A61B 6/06; A61B 6/4291; A61B 6/484; A61B 6/025; A61B 6/4014; A61B 6/4092; A61B 6/4233; A61B 6/583; A61B 6/4441; A61B 6/14; A61B 6/04; G06T 11/005; G01J 3/1256; G02B 21/0032; G02B 21/0064; G02B 21/0068; A61M 2205/3306; A61M 2205/3334; A61M 2205/50; A61M 5/16886; A61M 5/1689; A61M 5/1411; A61M 5/16804; A61M 5/16877; A61M 5/172; A61M 1/3627; A61M 2005/2407; A61M 2005/2488; A61M 2005/3125; A61M 2005/3126; A61M 2005/3152; A61M 2205/3553; A61M 2205/3561; A61M 2205/3592; A61M 2205/52; A61M 2205/8206; A61M 5/24; A61M 5/31535; A61M 5/31543; G01F 1/661; G01F 22/00; H04N 7/183; G05B 15/02

USPC ......................................... 378/4, 8, 9, 19, 62
See application file for complete search history.

(56) References Cited

U.S. PATENT DOCUMENTS

| | | | | |
|---|---|---|---|---|
| 4,101,370 | A * | 7/1978 | Russell | B27D 3/04 100/151 |
| 4,149,079 | A * | 4/1979 | Ben-Zeev | A61B 6/032 378/14 |
| 4,176,279 | A * | 11/1979 | Schwierz | A61B 6/027 378/19 |
| 4,178,511 | A * | 12/1979 | Hounsfield | A61B 6/032 378/12 |
| 4,266,136 | A * | 5/1981 | Duinker | A61B 6/032 378/21 |
| 4,637,040 | A * | 1/1987 | Sohval | A61B 6/032 378/10 |
| 6,819,736 | B1 | 11/2004 | Bruder et al. | |
| 7,073,939 | B2 * | 7/2006 | Spahn | G01N 23/04 378/189 |
| 8,279,996 | B2 | 10/2012 | Allmendinger et al. | |
| 8,306,304 | B2 | 11/2012 | Noo et al. | |
| 2009/0135995 | A1 * | 5/2009 | Eberhard | A61B 6/025 378/19 |
| 2010/0232565 | A1 * | 9/2010 | Ye | A61B 6/032 378/5 |
| 2012/0039434 | A1 | 2/2012 | Wang et al. | |

* cited by examiner

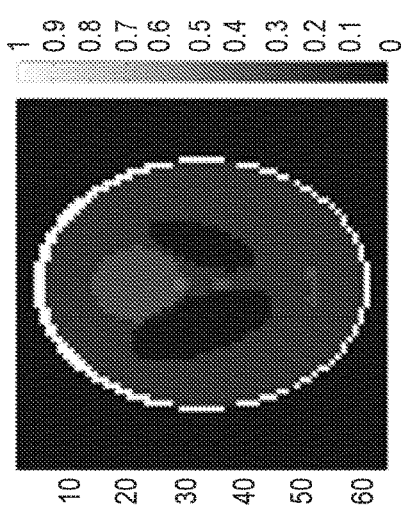
FIG. 6A
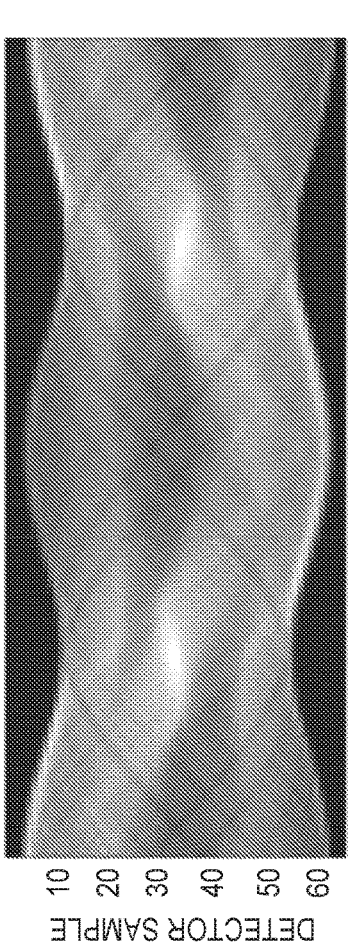
FIG. 6B
FIG. 6C
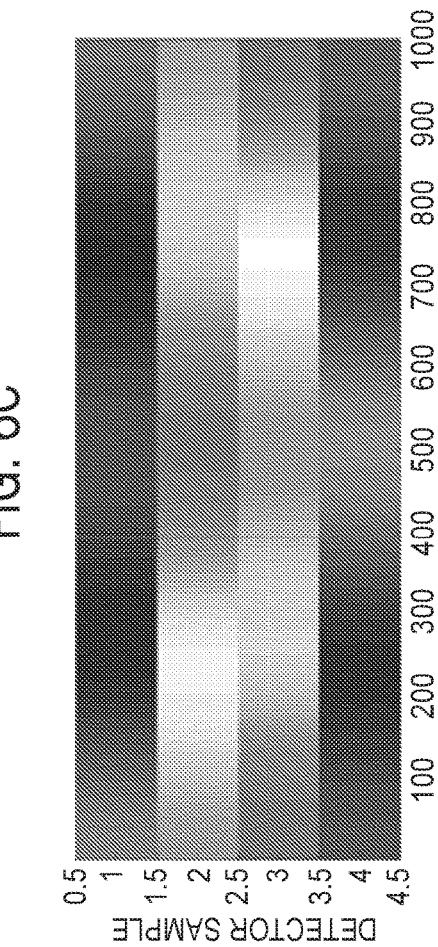
FIG. 6D
FIG. 6E

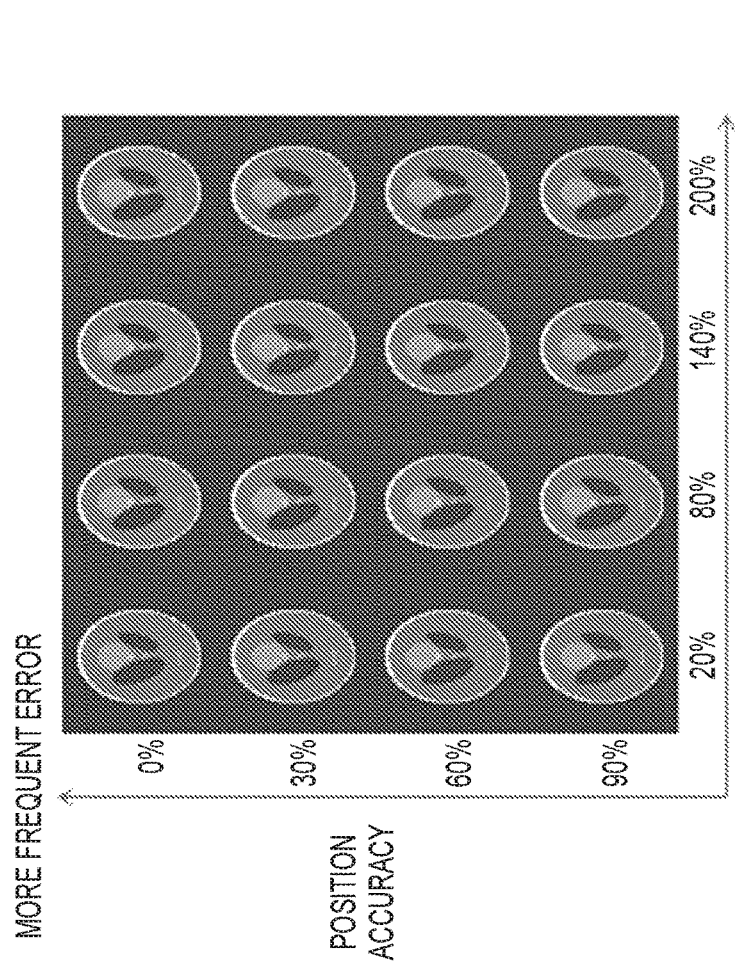
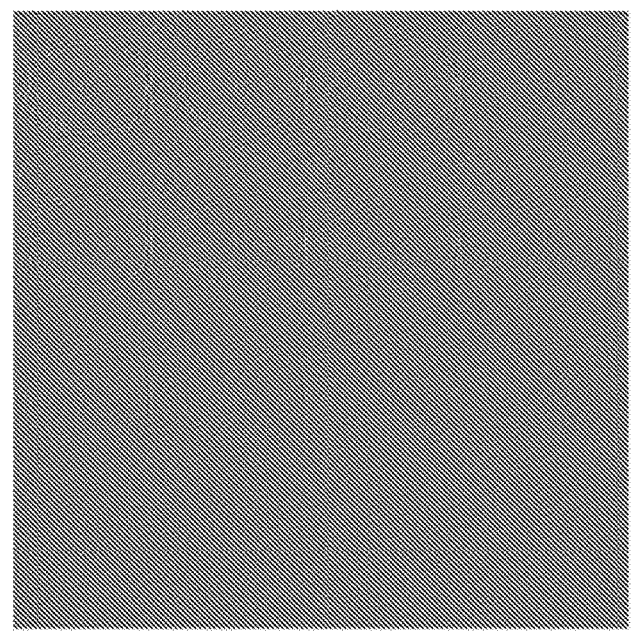
FIG. 11A
FIG. 11B

SYSTEM AND METHOD FOR ULTRA-HIGH RESOLUTION TOMOGRAPHIC IMAGING

CROSS-REFERENCE TO RELATED APPLICATIONS

This application represents the U.S. National Stage of International Application No. PCT/US2014/010307, filed Jan. 6, 2014 which is based on, claims priority to, and incorporates herein by reference in its entirety, U.S. Provisional Patent Application Ser. No. 61/749,151, filed Jan. 4, 2013, and entitled, "High Resolution Tomographic Image Reconstruction"

BACKGROUND OF THE INVENTION

The present disclosure relates generally to systems and methods for medical and security imaging and, in particular, to systems and methods for producing high-resolution tomographic images.

In past years, there have been many advances in the physics of medical tomographic imaging systems, one of the most notable being the advent of multi-detector row helical systems. Generally, the resolution of conventional tomographic systems has been driven by detector size and angular sampling. Historically, these quantities have been constrained to a regular polar coordinate grid sampling in Radon space, whereby higher resolution systems have required smaller, more expensive, detector elements and increasingly dense data acquisition systems, raising the cost and complexity for enhancing imaging capabilities.

Some techniques have been developed to improve sampling density, and thus achieve a higher resolution for existing CT systems. For example, in the quarter-detector off-set approach, the detector bank, which ordinarily is symmetric with respect to the line joining the x-ray source and the center of rotation, is offset the left or right, thereby providing extra additional views used to obtain supplementary information about the imaged object. However, for cone-beam scans and for spiral scans data redundancy from this approach is not really available since opposing rays do not coincide, but rather differ by tilt-angle with rotation and longitudinal position. Further, the quarter shift does not improve the sampling in the detector row direction, or longitudinal direction. Similarly, the flying focal spot (FFS) technique aims to increase sampling density by using periodic deflections of the focal spot in the in the radial direction and longitudinal direction. This approach can be used to double the sampling density in both directions regardless of the cone-angle and the spiral trajectory.

In addition to CT systems, a few approaches have been previously employed to achieve enhanced resolution in Positron Emission Tomography (PET) imaging. Some examples include using a combination of multiple low resolution images, dichotomic ring sampling, bed wobbling, and blurring kernel estimation on sinogram, to name a few. However, fundamental limits of spatial resolution in PET are related not only to the physical size of the detector or the non-collinearity of the detector geometry, but also to positron range modeling, detector cross-talk, and so forth. Approaches to overcome these limitations are still under investigation. Likewise, non-uniform sampling schemes based on general k-space trajectory studies and encoding methods have also been proposed for applications including magnetic resonance imaging (MRI) in order to improve acquisition speed or sampling density. These approaches aim to reduce data sampling and mitigate under-sampling artifacts and motion artifacts by combining non-uniform sampling with advanced reconstruction methods.

Therefore, given the above, there is a need for systems and methods for achieving ultra-high resolution imaging in tomographic systems.

SUMMARY OF THE INVENTION

The present invention overcomes the aforementioned drawbacks by providing a system and method directed to reconstructing tomographic images acquired with relatively large detectors, providing for improved resolution using iterative reconstruction techniques. Specifically, the present invention includes shifting a detector or radiation source by a shift value at each angular sampling during an acquisition process, thereby allowing for increased resolution and accuracy compared to a conventional fixed detector or source approaches. As an example, the shift value may be a fractional shift that is defined as a fraction of the detector size. In addition, the present invention provides a reconstruction to precisely model the fractional shift of a detector, implemented with an Iterative reconstruction formula.

In one embodiment of the present invention, a method for producing an image of a subject with a tomographic imaging system is provided. The method includes directing a tomographic imaging system to rotate a radiation detector through a plurality of angular positions around a subject. The method also includes acquiring data with the tomographic imaging system by directing the tomographic imaging system to shift the radiation detector by a different shift value at each angular position, and reconstructing an image of the subject from the acquired data.

In another embodiment of the present invention, a tomographic imaging system is provided. The system includes a gantry configured to rotate about a rotation axis, a detector system coupled to the gantry and configured to detect radiation incident on the detector system and a controller. The controller is configured to direct the gantry to rotate the detector system through a plurality of different angular positions, and shift the detector system by a different shift value at each of the plurality of different angular positions.

The foregoing and other advantages of the invention will appear from the following description.

BRIEF DESCRIPTION OF THE DRAWINGS

FIG. 6 shows a sinogram comparison from two detector sets, in accordance with the present invention;

FIG. 11 shows reconstructed images and error maps using shift perturbations, in accordance with the present invention;

DETAILED DESCRIPTION OF THE INVENTION

Described here are systems and methods for acquiring high-resolution data with a tomographic imaging system using fractional positional shifts of system detectors or detector arrays. For instance, the systems detectors or detector arrays may be shifted as they are rotated about an object being imaged such that data is acquired along a spiral sampling pattern that is formed on a polar coordinate Radon space. As an example, the spiral sampling pattern may be a non-uniform spiral sampling pattern, such as an Archimedean spiral. A model-based reconstruction approach can then be used to achieve superior image resolution, as will be described. Using an accurate system model, ultra-resolution properties of a resulting system are demonstrated, with application to stationary or fixed trajectory tomographic systems, such as SPECT, PET, circular trajectory CT, and fixed pitch helical CT, to name a few.

Figure 1A:
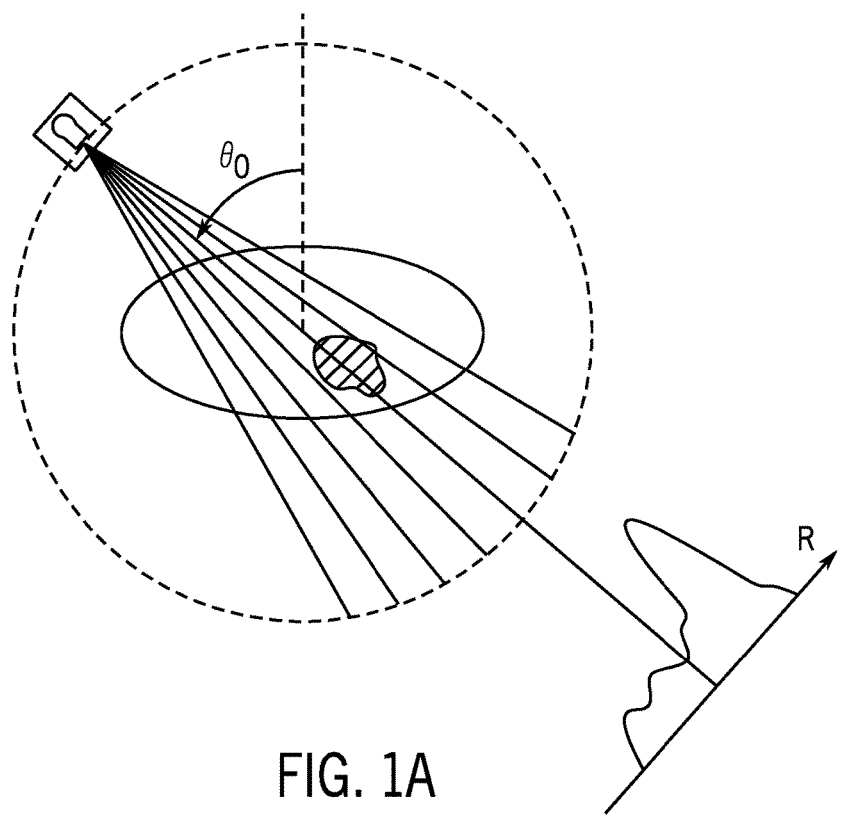
FIG. 1A is a pictorial representation of data acquisition in a parallel beam computed tomography imaging system.
Figure 1B:
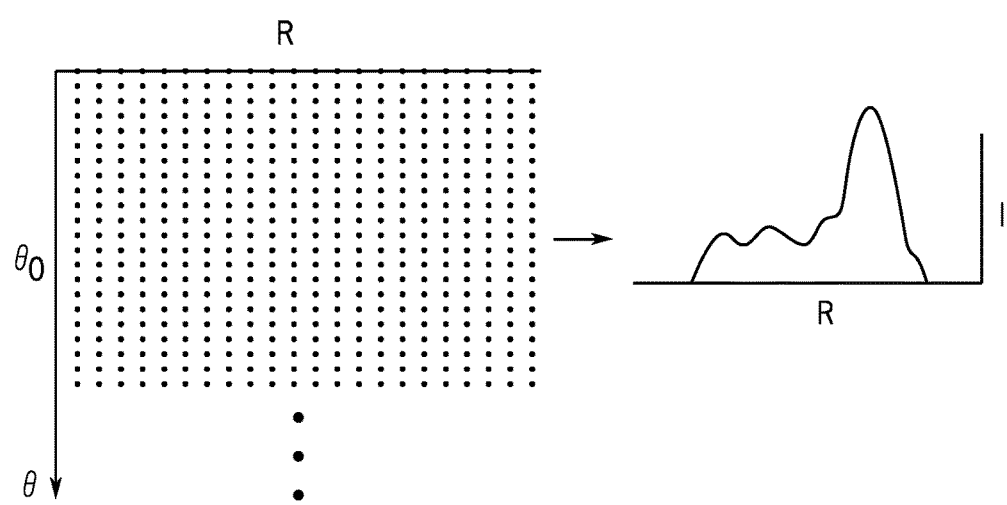
FIG. 1B is a pictorial representation of a plot of attenuation coefficient values along the projection view of FIG. 1A.

First, by way of example, a review of conventional data acquisition for an x-ray computed tomography ("CT") system is provided. The data acquire with such a system can include a set of projection views all acquired at the same axial position, $z_0$. As shown in FIG. 1A, in this example, each projection view is acquired at a specific view angle, $\theta$, and each detector attenuation measurement is at a location, R, in a detector array. As shown in FIG. 1B, the image data may be stored in a two dimensional array called a "sinogram." One dimension of the sinogram corresponds to the angular position of the fan beam, or view angle, $\theta$. The other dimension corresponds to positions of the detector elements, R, of the detector array. As the detector array in a fan beam CT system generally includes a single row of detector elements, each row of the sinogram corresponds to a discrete view angle, $\theta$, and a single axial position, $z_0$.

A sinogram obtained in this manner is a collection of projection views of the subject at the position, $z_0$. In general, a projection view is a row of projection data corresponding to a given view angle, $\theta$, and representing the imaged subject at a single axial position, $z_0$. Well known tomographic image reconstruction procedures utilize as their principal inputs a complete set of such projection views (discretized in $\theta$, but all containing data values for the same axial position, $z_0$). The projection views are processed by such tomographic techniques to reconstruct a slice image depicting the internal features of the subject in a slice located at the position, $z_0$.

FIG. 1A illustrates the correspondence between a particular view angle, $\theta_0$, for the x-ray source and the generation of a well defined row, R, of projection data. In the fan beam case, as noted above, the detector data from the detector array may convert directly into a single row of projection data for a projection view at view angle, $\theta$. This correspondence results because the detector array provides a single row of detector data representing intensities, I, of the x-rays impinging upon the detector elements. These intensity values, I, indicate attenuation information for the subject at the axial position, $z_0$.

FIG. 1B shows how the projection data for the particular view angle, $\theta$, is stored in a corresponding row of the sinogram. Each row of this sinogram thus constitutes a projection view that indicates attenuation information, I, for a distinct view angle, $\theta$, at the same axial position, $z_0$. The integral value, $p_0$, of the intensities, I, along a projection view that corresponds to a particular view angle, $\theta_0$, has the form $p = \int_{\theta_0} \mu(x) dx$, where $\mu(x)$ is the attenuation coefficient at a point x along the projection view.

In the following, a general Archimedean spiral is reviewed, and an exact formulation for an approach implementing fractional shifts of detectors with the modified Archimedean spiral is developed. In addition, an iterative image reconstruction method is examined and a demonstration for significant resolution improvement in accordance with the present invention is shown using 2D simulation data and 3D helical cone beam clinical data.

Figure 2:
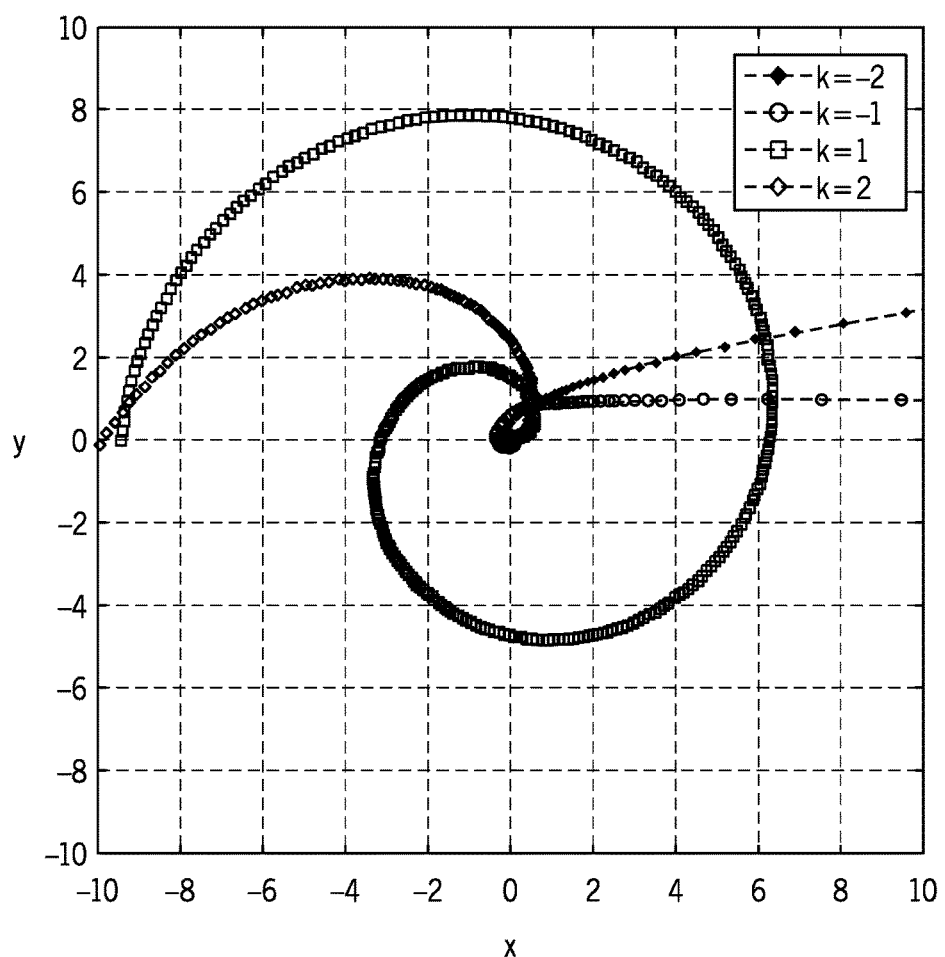
FIG. 2 is graphical illustration of several generalized Archimedean spirals, in accordance with the present invention.

The Archimedean, or arithmetic, spiral ("AS") is the locus of points corresponding to the location of a point rotating at a constant angular velocity and moving away from a fixed origin with a constant speed along a line over time. In a generalized Archimedean spiral, the radial distance, r, varies according to the following function:

$$r = a + b\theta^{1/k} \qquad (1)$$

where $\theta$ is the polar angle, and a and b are parameters, which may be constant. As k is modified, for example, from $-2$ to 2, the resulting spirals wrap more tightly. FIG. 2 shows the trajectory of $(\theta, r)$ on a Cartesian grid for several values of k, with $a=0$ and $b=1$, and $0 \leq \theta \leq 540°$.

Figure 3A:
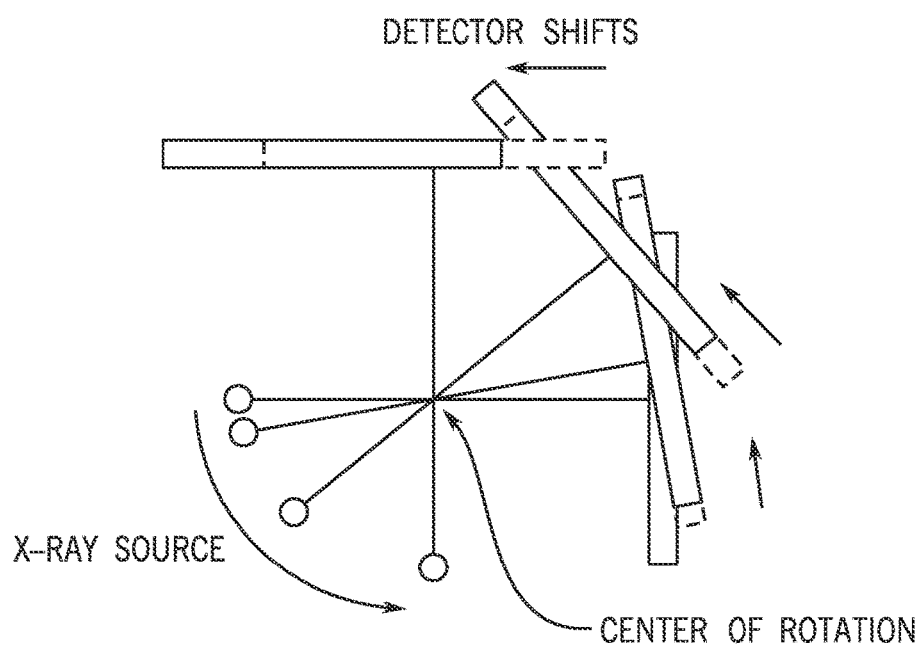
FIG. 3A is a diagram illustrating the application of fractional shifts to a radiation detector for use in a system in accordance with some embodiments of the present invention.

In some aspects of the present invention, a trajectory described by Eqn. 1 may be used as a sampling pattern in tomographic systems configured for shifting a detector array any amount of shift values at different angular positions. In certain preferred configurations, shift amounts may be a variable fraction of a detector size in dependence of an angular sampling position. A schematic diagram of such fractional shift pattern is illustrated in a diagram shown in FIG. 3A. For example, shift amounts may be 1 n for each n angular sampling positions, that is, at each position, a detector system may shift a detector array by an amount defined by the polar angle, θ, to create an Archimedean spiral pattern on the polar coordinate Radon space, whereby the resulting sampling trajectory can be interpreted in the sinogram domain (i.e., Cartesian coordinate Radon space).

Figure 3B:
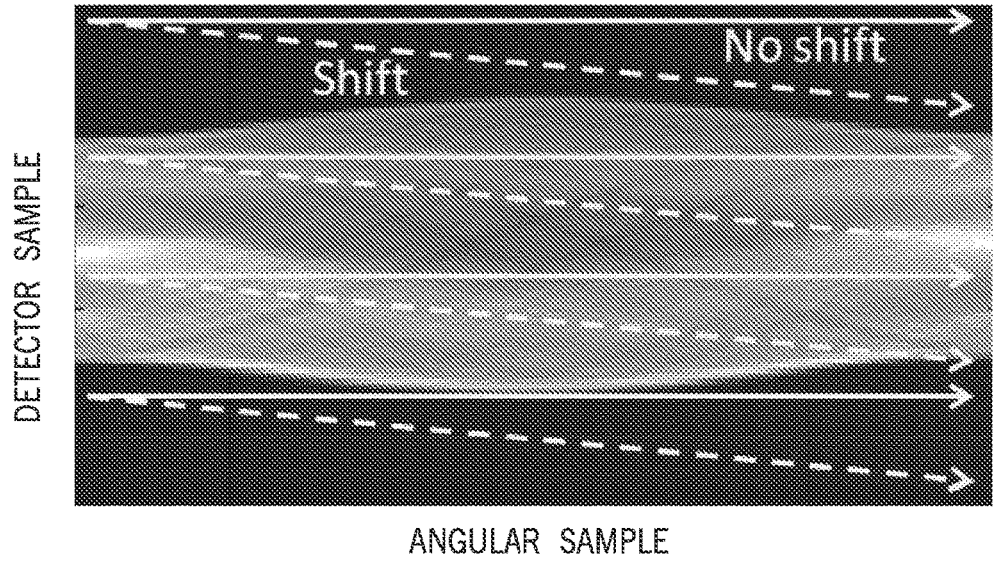
FIG. 3B shows a comparison of detector sampling trajectories in the sinogram domain using a detector system in accordance with the present invention.

FIG. 3B shows a comparison of detector sampling trajectories in the sinogram domain resulting from data being acquired in accordance with some embodiments of the present invention. In 3B, sampling trajectories for which the detector is not shifted are shown as horizontal solid lines whereas sampling trajectories for which the detector is shifted are shown as tilted dashed lines. As seen in FIG. 3B, the dashed lines make it possible to acquire sub-detector pixel information for each view, and are equivalent to arithmetic spirals in a polar coordinate Radon space.

In some configurations, an irregular sampling pattern on the polar coordinate Radon space may be achieved for any detector element in a detector array, and may be described using a modified Archimedean spiral, as follows:

$$r = a + \left(\frac{b'}{2n}\right)\theta^{1/k} \quad (2)$$

where a is the initial detector location; b' is the normalized detector span pitch, namely how many detector elements are shifted after a 360 degree rotation; and n is the total rotation (i.e., the rotation/180 degree). In Eqn. 2, a value of k=1 may be used, but this value may be modified. The modified AS, as shown, may easily model multiple spirals from multiple detector elements using any combination of parameters, as desired. For example, for a=0, a spiral pattern starts from (0,0), while for a=1, a spiral pattern starts from (1,0). Next, b' defines the amount of total shift, normalized by a single detector element. For example, when b'=1 and the size of the detector element is 10 mm, the total fractional shift covers 10 mm, while when b'=1.25, the total fractional shift becomes 12.5 mm. Furthermore, in the case that a 360 degree rotation scan is desired, n may become 2, since n=360/180=2.

Figure 3C:
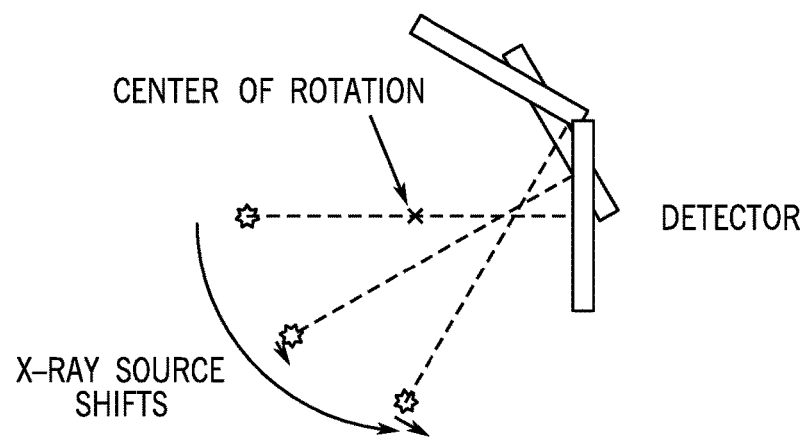
FIG. 3C is a diagram illustrating the application of fractional shifts to a radiation source for use in a system in accordance with some embodiments of the present invention.
Figure 3D:
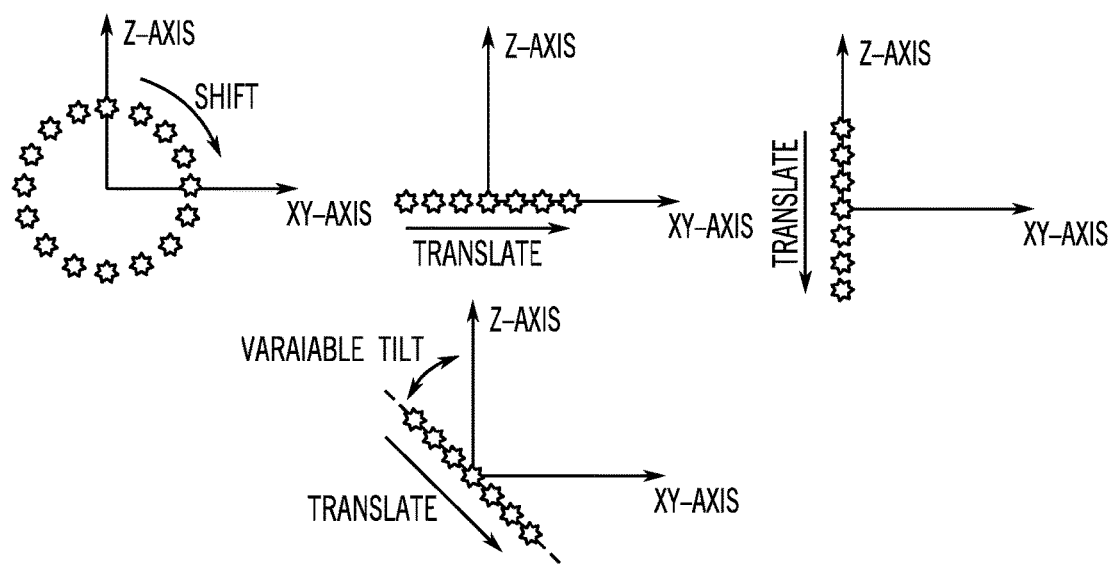
FIG. 3D is a diagram illustrating some examples of radiation source shift patterns that can be implemented in some embodiments of the present invention.
Figure 4A:
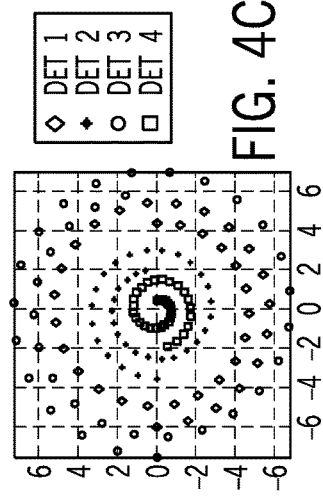
FIG. 4 shows examples of Archimedean spirals on Radon space generated using different parameters, in accordance with the present invention.
Figure 4B:
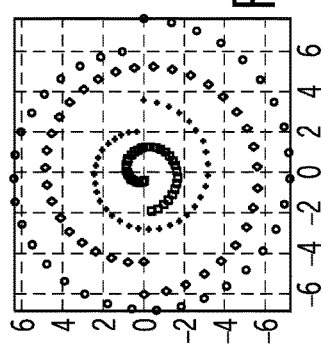
Figure 4C:
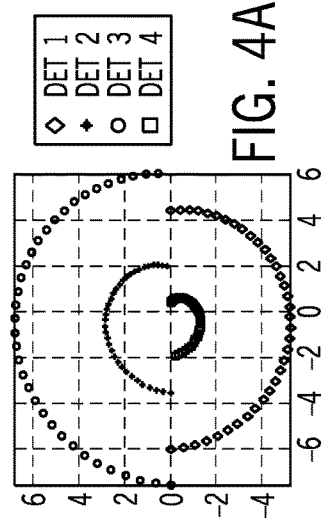
Figure 4D:
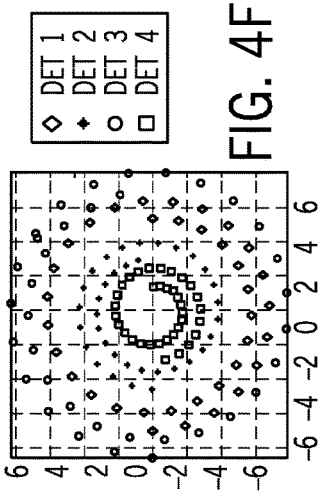
Figure 4E:
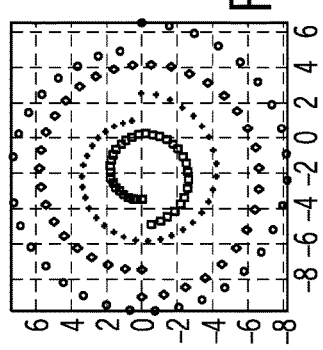
Figure 4F:
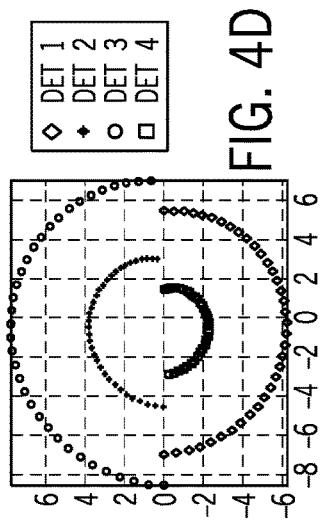
Figure 4G:
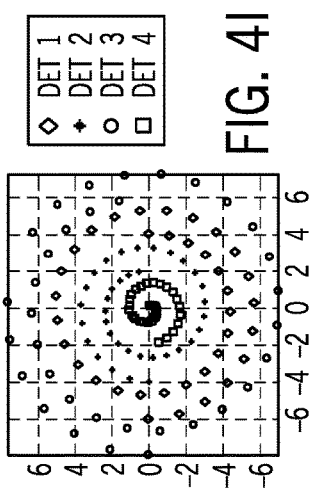
Figure 4H:
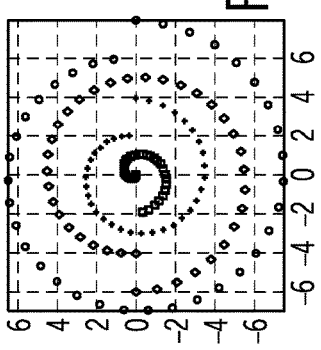
Figure 4I:
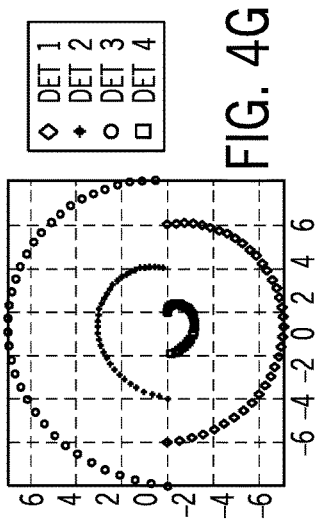

As illustrated in FIG. 3C, in some embodiments the radiation detector is not shifted, but the radiation source is shifted to achieve the spiral sampling on the polar coordinate Radon space. As an example, the radiation source can be shifted mechanically as it rotates about the object being imaged. As another example, the radiation beam can be electromagnetically steered so as to achieve and effect shift of the radiation source relative to the non-shifted radiation detector. As illustrated in FIG. 3D, the radiation source can be shifted in any number of a different patterns, such as linearly along one direction, linear along a tilted axis, or in another pattern, such as being shifted to wobble around a center of rotation.

FIG. 4 illustrates a variety of Archimedean spiral trajectories described by different parameter values. Each plot of FIGS. 4 (a), (b), (c), shows several trajectories obtained for parameter values a=[−6, −2, 2, 6], with b'=1 and different n values, namely n=1, 2, and 3, respectively. When initial detector locations are changed according to the values a=[−7, −3, 3, 7], the modified Archimedean spiral trajectories draw spirals from the initial locations of each element as shown in FIGS. 4 (d), (e), and (f). Such initial location changes may be applicable for the configurations implementing inhomogeneous detector elements.

As may be appreciated, the approach of the present invention, as described, may be modified using appropriate parameter selections to produce effects similar to those using a quarter-detector off-set method, a method usually used for improving spatial sampling pattern in conventional geometry systems. For example, by changing the normalized detector span pitch b', similar patterns are observed, as shown in FIG. 4. Specifically, plots of FIGS. 4 (g), (h) and (i) were obtained using a=[−6, −2, 2, 6], with b'=1.25 and different n values, namely n=1, 2, 3, respectively, where b' was selected to generate spiral sampling patterns that are more evenly spread out.

The Archimedean spiral on Radon space ("ASRS") method described here may be implemented in accordance with an accurate system-modeling approach for generating images, which accounts for all details of detector element locations, detector system motion, and source location. Specifically, a system matrix, H, may be formulated by a modified AS and an energy functional defined as follows:

$$J_p(x) = \|y - Hx\|_2^2 + \lambda^2 \|Dx\|_p^p \quad (3)$$

where D is the discrete approximation to the gradient operator, λ is a regularization parameter, and p is the power of the L-p norm, (i.e., $$\left(\text{i.e., } \|z\|_p^p = \sum_{i=1}^{n} |z_i|^p\right).$$

Figure 5:
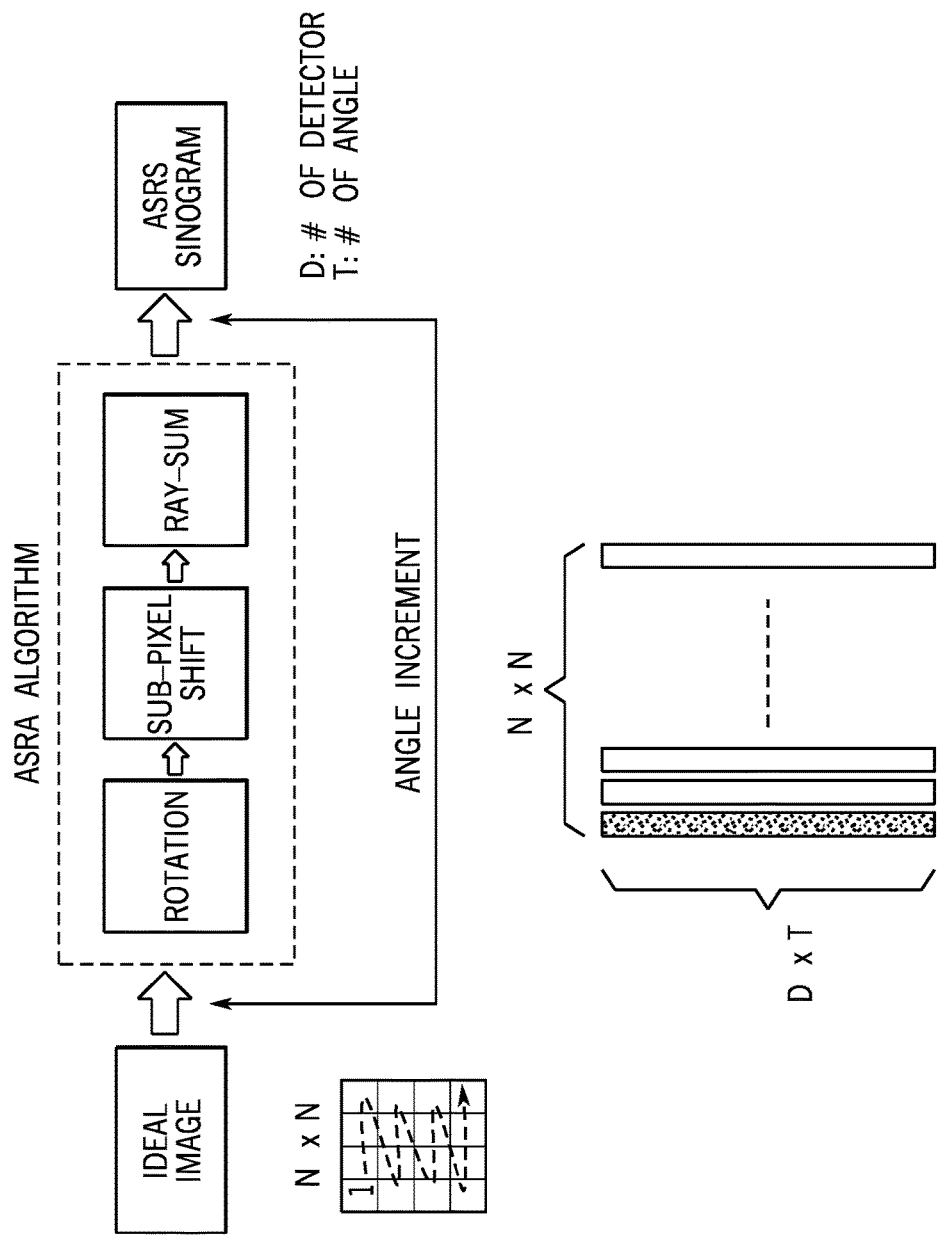
FIG. 5 is a flowchart schematic illustrating the steps of constructing a system matrix for ASRS with a fractional detector shifting method, in accordance with the present invention.
Figure 7C:
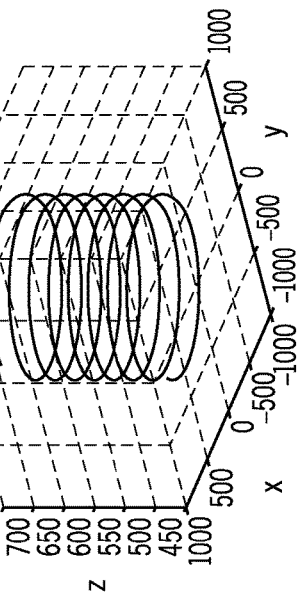
FIG. 7 is a graphical illustration representing a configuration of Archimedean spiral method on helical cone beam CT with a small-step flying local spot model, in accordance with the present invention.
Figure 7E:
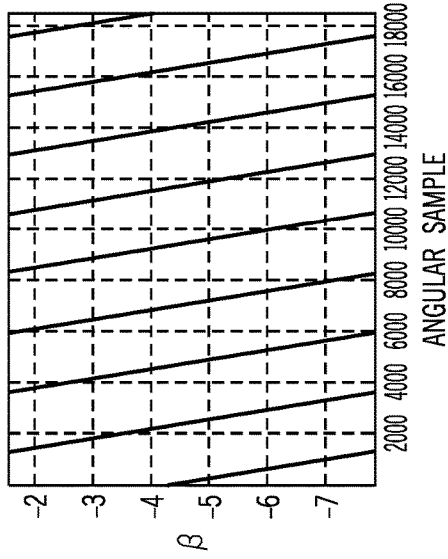
Figure 7B:
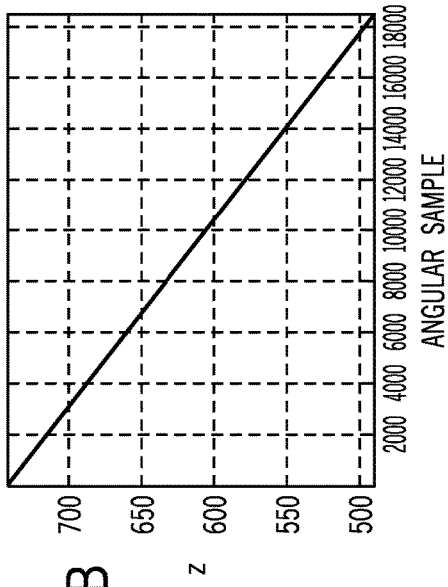
Figure 7D:
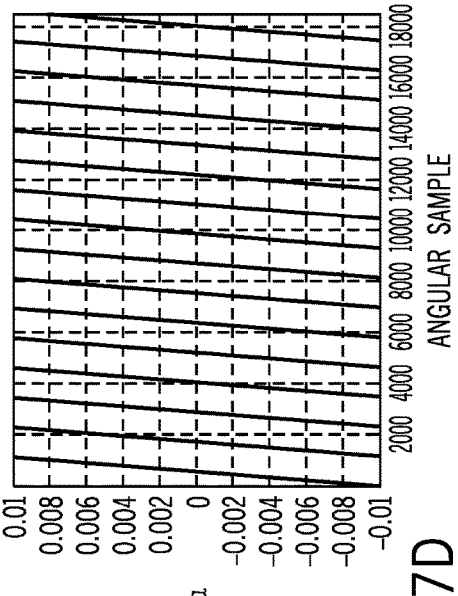
Figure 7A:
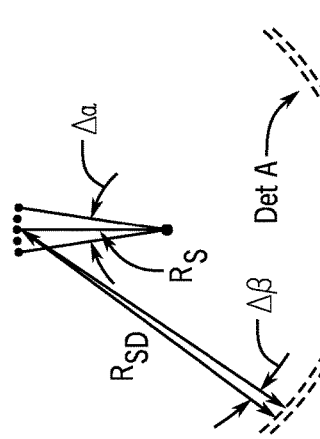

A generalization of a method for generating the system matrix that incorporates the shifted radiation detector, source, or both, is illustrated in FIG. 5.

Thus, the system fidelity term is L-2 norm and the smoothness penalty function is L-p norm. To alleviate the non-differentiability at the origin (except for p=2), very small constant (β>0) may be used for the approximation near the origin:

$$\|Dx\|_p^p \approx \sum_{i=1}^{n} (|Dx|_i^2 + \beta)^{p/2} \quad (4)$$

The energy functional can then be expressed by:

$$J_p(x) = \|y - Hx\|_2^2 + \lambda^2 \sum_{i=1}^{n} (|Dx|_i^2 + \beta)^{p/2} \quad (5)$$

which may be minimized with respect to with the solution given by the following linear normal equation:

$$(H^T H + \alpha^2 D^T W_x D)x = H^T y \quad (6)$$

where $$W_x = \text{diag}\left(\frac{p/2}{(|Dx|_i^2 + \beta)^{1-p/2}}\right) \quad (7)$$

For example, when p=1 and β=1×10⁻⁵, this Eqn. 6 becomes a type of Total Variation (TV) image reconstruction formulation, which has been shown to generate robust images for sparse angular view reconstruction approaches. This same idea may be extended in the approach of the present invention to show that the sparse detector sampling can be overcome by the integration of detector motion, accurate system modeling, and TV regularization based iterative image reconstruction.

The above-described systems and methods may be further understood by way of examples. These examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims. For example, suitable results may be achieved if the described techniques are performed in a different order and/or components in a described system, architecture, device, or circuit are combined in a different manner and/or replaced or supplemented by other components or equivalents. Likewise, specific process parameters and methods are recited that may be altered or varied based on any number of variables.

Example 1

Conventional tomographic reconstruction methods rely on regular, uniform sampling, and thus cannot be used in the non-uniform sampling approach of the present invention. A model-based iterative image reconstruction approach was used to demonstrate enhanced reconstruction resolution using a generated Archimedean spiral sampling pattern on Radon space. Two approaches were introduced, where one was based on the fractional shifts of the system detectors and the other on the fractional shifts of the source, which can be achieved by modifying the flying focal spot motion, allowing a view-by-view deflection of the focal spot.

Simulation results demonstrated a many-fold resolution improvement in parallel beam geometry. Gaussian noise was simulated on a sinogram and the optimum reconstruction parameters were sampled for the fractional detector motion case. Results indicated that the regularization parameters were dependent upon the noise level for optimal image reconstruction. In addition, perturbation of detector shift motion was another potential source of error, which was simulated by changing the magnitude and frequency of perturbations. Results also showed step size perturbations up to 200 percent may be acceptable if the frequency of perturbation is low (e.g., less than 10 percent shifted positions in errors). In addition, the approach of the present invention was applied to helical cone-beam multi-row detector CT ("MDCT") configurations by modifying the flying focal spot motion instead of the detector motion, thus demonstrating its application to current commercial systems.

2D Simulation

Fractional Detector Shifting

An iterative image reconstruction method was performed by generating a system matrix for a fractional shifting realization of ASRS in a 2D simulation implementing the fractional detector shifting method, as described. The ASRS projection algorithm consisted of rotation, sub-pixel shift, and ray-sum functions (as shown in FIG. 4). These functions were repeated to construct an ASRS sinogram by changing the initial locations and rotation angles of the detector system, as previously described. A ASRS sinogram was generated for a 64×64 ideal image by using a number of detectors (I)), namely, D=4, and a number of angles (T), namely T=1024. For comparison, a sinogram was also generated using a conventional program without the proposed sub-pixel shift, with D=64 elements.

Turning to FIG. 6, a visual comparison between the two sinograms is shown. Specifically, FIG. 6 (c) shows the conventional sinogram collected using a 64-element detector system and FIG. 6 (e) shows the sinogram collected using a 4-detector element detector system with fractional shifts, in accordance with the present invention. In this experiment, it was demonstrated that the ASRS method can overcome conventional beliefs that the size of a detector element limits the image resolution in tomographic systems.

Although many parameters may be changed, control parameters were kept for this experiment to show the efficacy of ASRA. Specifically, parameters were chosen to show up to 16-fold resolution improvement (see FIGS. 6 and 8). Firstly, enough angular measurements to make the number of equations and unknowns equal were collected. There were 4096 (=64×64) unknowns and 4 sensors used in this setup; hence 1024 angular views were collected in all. Secondly, the detector linear motion was encoded to generate an Archimedean spiral, as shown in Eqn. 2 above, with b=1, a=[−6, −2, 2, 6], and 0=360. Thirdly, the images were reconstructed using a Matlab code with matrix form for the system matrix and vector forms for image and sinogram, as shown in Eqn. 6 above. Building an accurate system matrix required up to one hour of processing without parallel implementation, but the image reconstruction time was less than one minute using a 64-bit Windows-7 OS with a 16 GB memory. Moreover, once the system matrix was calculated and saved, it could be used repeatedly.

3D Simulation

Small-Step FFS

In a different experiment, a 3D simulation was performed using an ASRS approach as would be used on a helical cone beam clinical scanner (e.g., a. Brilliance CT 64, Philips Healthcare, Cleveland, Ohio, USA). Instead of modeling a detector system motion, we performed a simulation using a changing focal spot model. Specifically, a small-step flying focal spot (FFS) was used, which allows for view-by-view deflections of the focal spot moving at a slow rate. This is a source motion encoding method compared to the detector motion encoding approach as described in the previous 2D simulation example. Both approaches generate similar spiral sampling patterns on Radon space even though it may be more difficult to visualize spiral patterns in the 3D case.

FIG. 7 (a) shows a diagram for a small-step ITS, illustrating the rotation of the X-ray focal spot with respect to $\Delta\alpha$. The system geometry was defined according to $R_S$=570 mm, $R_{SD}$=1040 mm, equiangular focal spot deviation, $\Delta\alpha$=0.02 radian, and equiangular detector deviation, $\Delta\beta$=0.014 radian. There were 64 detector rows and 672 detector channels in the original system. We combined three detector channels to make a bigger detector channel in our model, thus using 226 channels in this 3D simulation with the same detector coverage. The Z-location of the X-ray source is shown in FIG. 7 (b), the gantry rotation (13) at the center of the detector system is shown in FIG. 7 (c), the Small-step FFS parameter (a) with 1160/2π is displayed in FIG. 7 (d), and the 3D source trajectory constructed is shown in FIG. 7 (e). All parameter selections were chosen to replicate those of a typical clinical scanner, except for the additional small-step FFS model ($\alpha$) and detector element pitch, which was three times larger. In summary, focal spot motion was encoded with a small-step ITS and used only ⅓ of detector elements, which were three times bigger than the original detector elements. The data collection diameter, or field of view (500 mm), was identical to the field of view of the original scanner. The raw data from the scanner was used to reconstruct the initial image.

Fractional Detector Shifting for ASRS

Figures 8A, 8B, 8C:
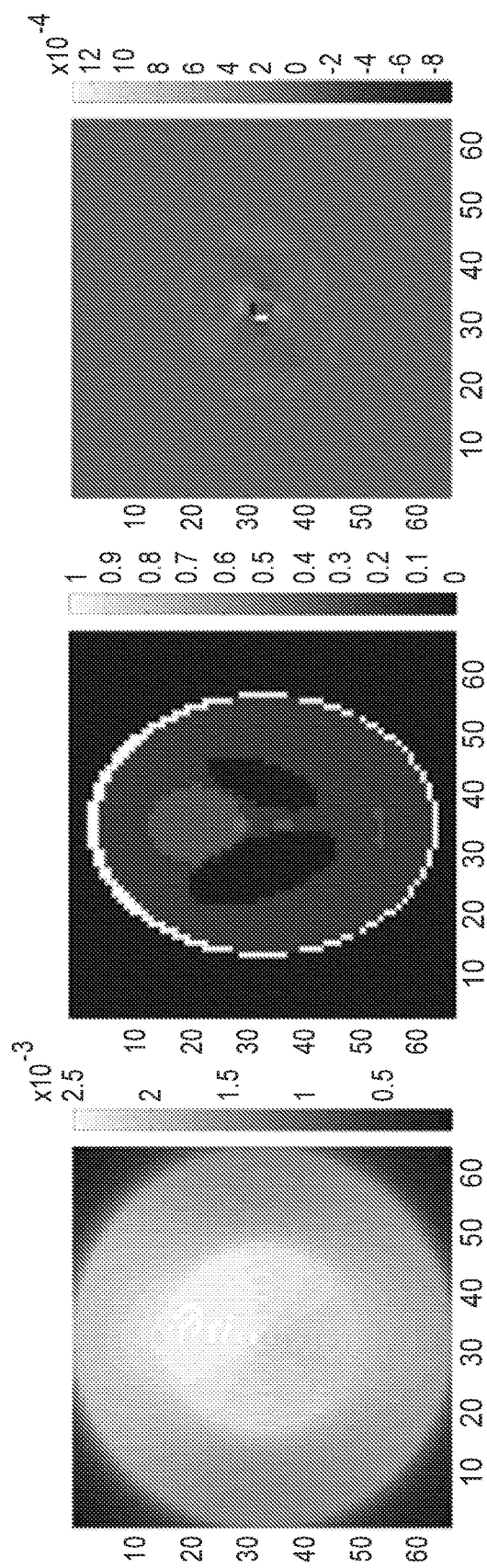
FIG. 8 shows a reconstructed image comparison using a compressed sinogram, in accordance with the present invention.

The sinogram generated by bigger detector elements appears similar to a "compressed version" of the normal sinogram. This compressed sinogram has an under-sampling effect in the azimuthal direction, and as a result, the image reconstructed from the compressed sinogram using a conventional TV method without shift modeling in the system matrix results in a blurred image, as shown in FIG. 8 (a). By contrast, the reconstructed image in FIG. 8 (b) that uses the same compressed sinogram data and incorporates the fractional shifts in the system model shows an almost identical image resolution compared to that of the ideal image from FIG. 6 (a). FIG. 8 (c) illustrates the error map between the ideal image of FIG. 6 (a) and the reconstructed image of FIG. 8 (b). In this case, the mean squared error (MSE) was 0.0092 (i.e. units=µ: a linear attenuation coefficient).

Figure 9:
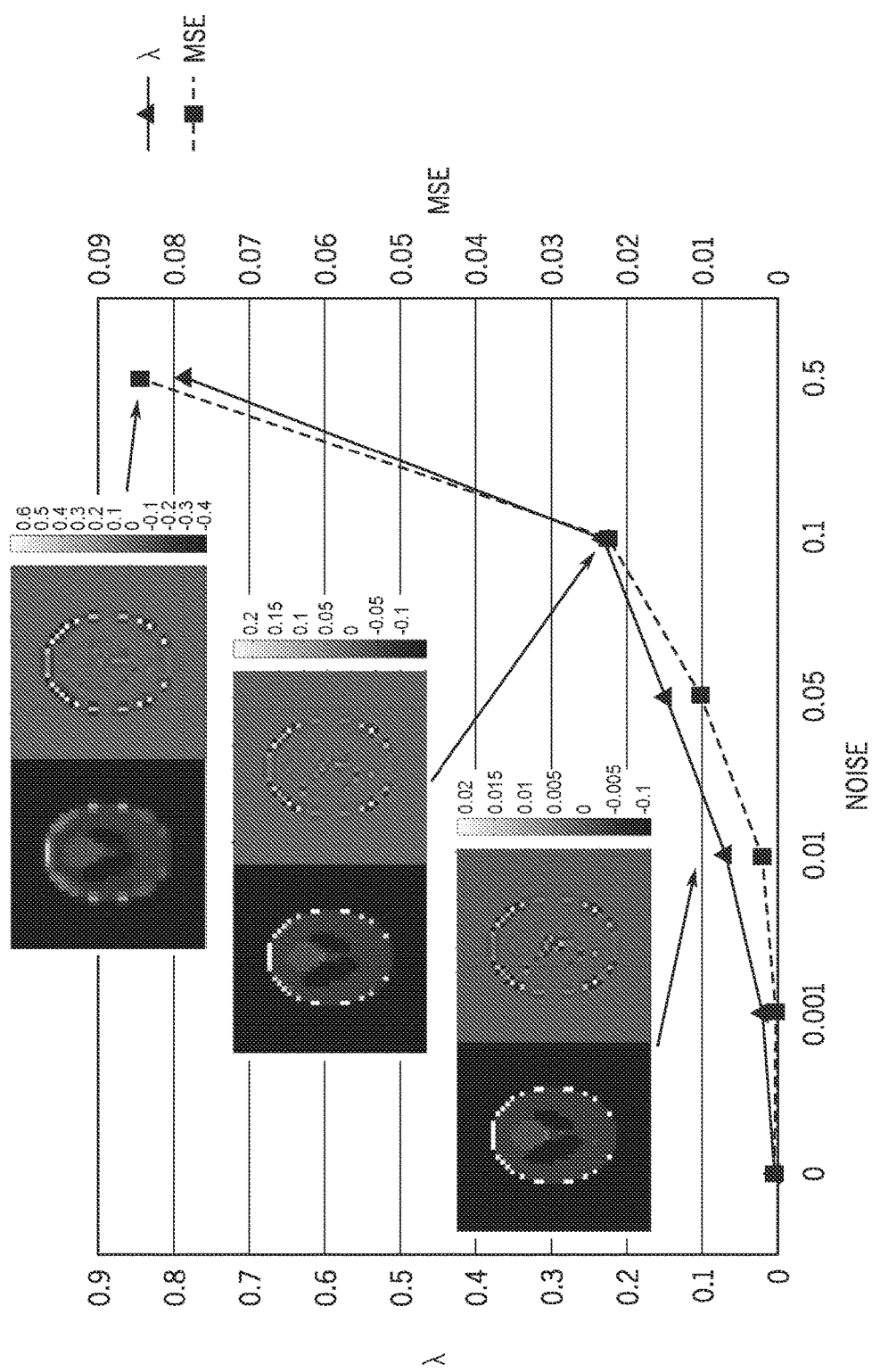
FIG. 9 is a graphical illustration representing noise effects and parameter selection, in accordance with the present invention.

To investigate the effect of noise and parameter selection, the variance in Gaussian noise was modified to simulate noise on the sinogram, and the regularization weight ($\lambda$) in Eqn. 5 above was assigned a value between (0, 1), where the total counts of dose of measurement were not considered. For each case, a line-search was performed to find the optimum $\lambda$ for minimizing MSE. As expected, the regularization weight increased with noise, and so could be pre-calculated by measuring the sinogram domain noise. The reconstructed images and error maps are also depicted in FIG. 9.

When projections are acquired using an Archimedean spiral trajectory, the position of a real scanner may be affected by mechanical or electronic perturbations. Thus, although an image reconstruction algorithm would assume a pre-defined spiral trajectory as a sampling trajectory, a real measurement would be subject to slight variations, which could cause error in the reconstructed images. Therefore, perturbations of detector shifts were simulated using two random number generators, namely one for the magnitude of perturbation and the other for the frequency of perturbation. The first generated a normal Gaussian distribution with N(0, $\sigma$), with the mean noise set to be zero. The standard deviation of noise ($\sigma$) was normalized by the step size of the detector shift ($\Delta$). The Noise Standard Deviation/Step Size (NSD/SS) was calculated using $\sigma/\Delta*100$. The second random number generator controlled where noise was added to the ideal shift. A Position Accuracy Ratio (PAR) was used to determine how many positions would be affected by noise (or perturbation). For example, PAR=30% meant that the 30% of sampling positions were accurate. In other words, 70% of sampling positions would be corrupted by the addition of noise generated by the first random number generator.

Figure 10:
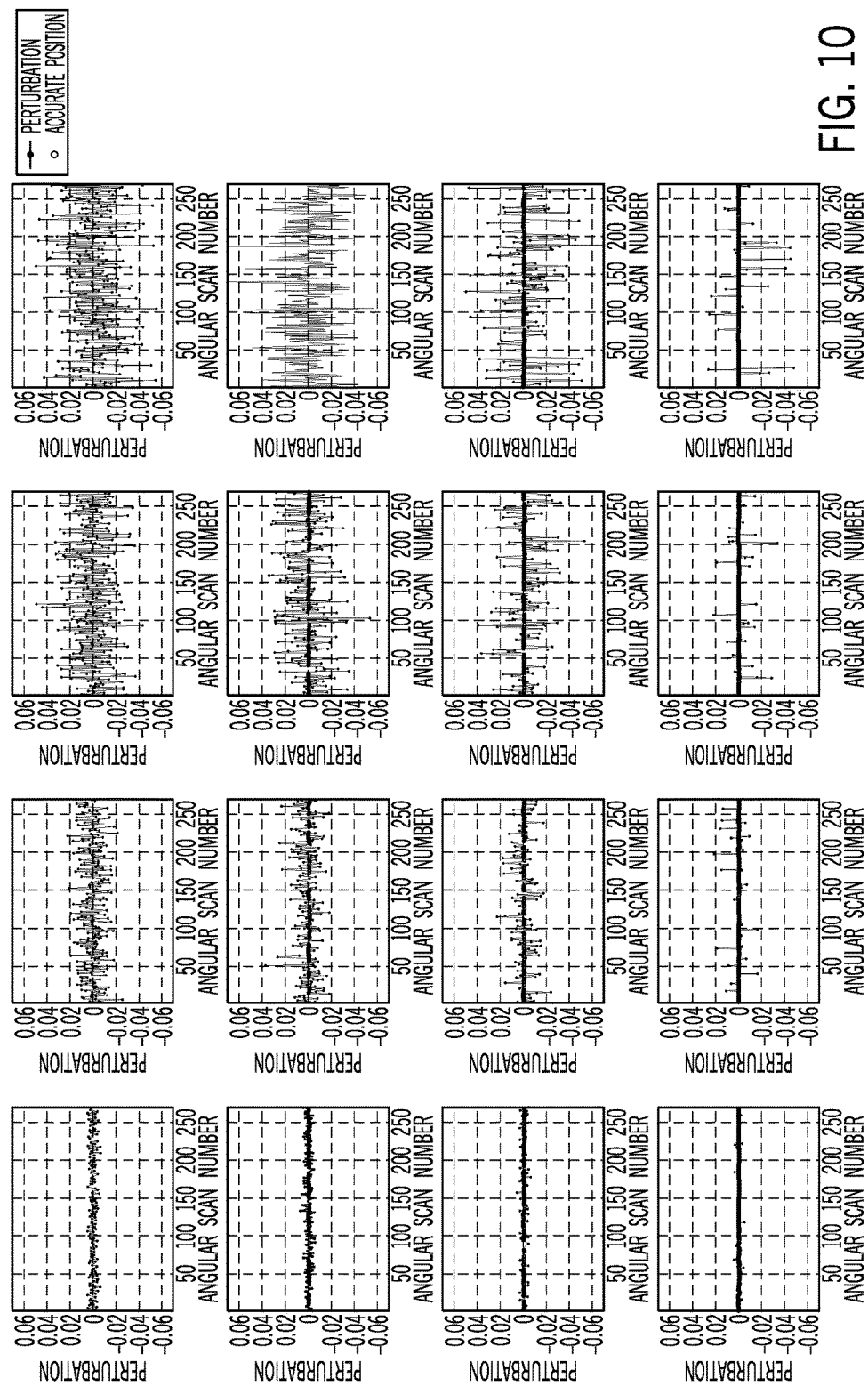
FIG. 10 is a graphical illustration representing perturbation simulation results, in accordance with the present invention.

The simulation was performed using a phantom image (90×90) with 30 detector elements. The size of each detector element was three times bigger than the image pixel size. Angular scans included 270 positions with step size determined according to $\Delta$=(Detector size)/(# of angular scan) namely 3/270=0.0111. FIG. 10 shows the generated perturbation patterns using multiple values for NSD/SS, namely 20%, 80%, 140%, and 200%, and multiple values for PAR, namely 0%, 30%, 60%, and 90%. In FIG. 11, the reconstructed images using the above perturbations are displayed along with the corresponding error maps are displayed.

Figure 12:
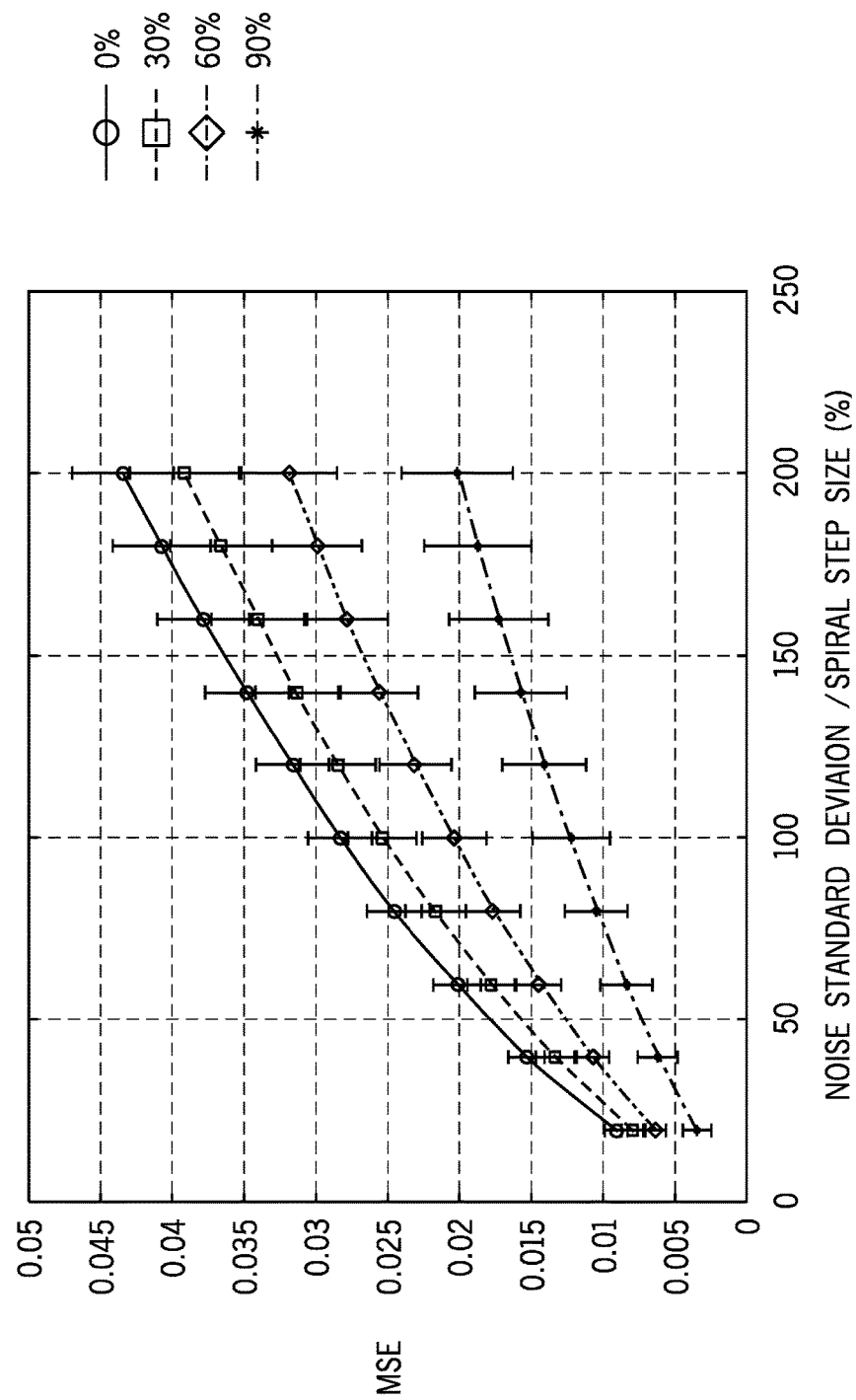
FIG. 12 is a graphical illustration representing perturbation simulation results with two random number generators, in accordance with the present invention.
Figure 13A:
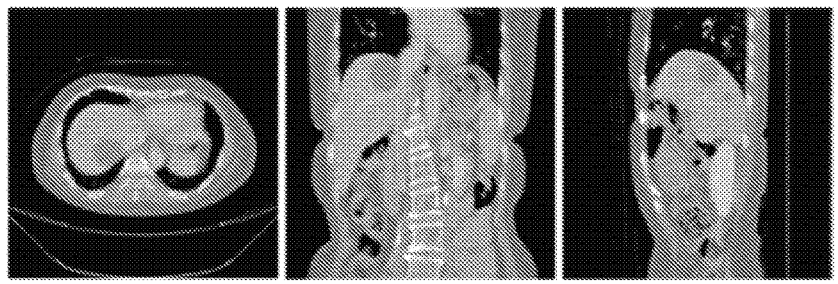
FIG. 13 shows a comparison of example reconstructed images, in accordance with the present invention.
Figure 13B:
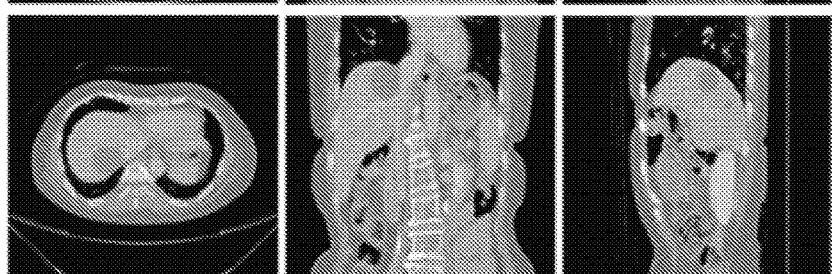
Figure 13C:
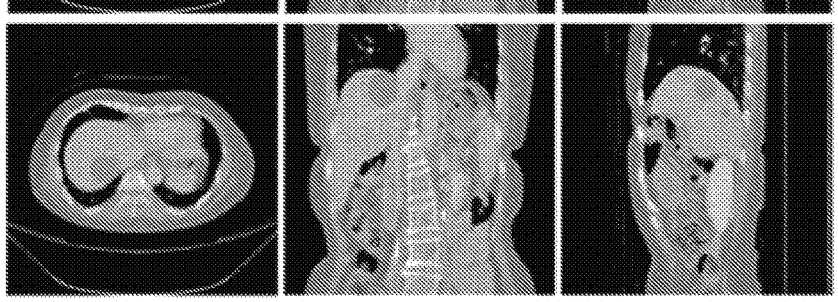
Figure 13D:
Figure 13E:
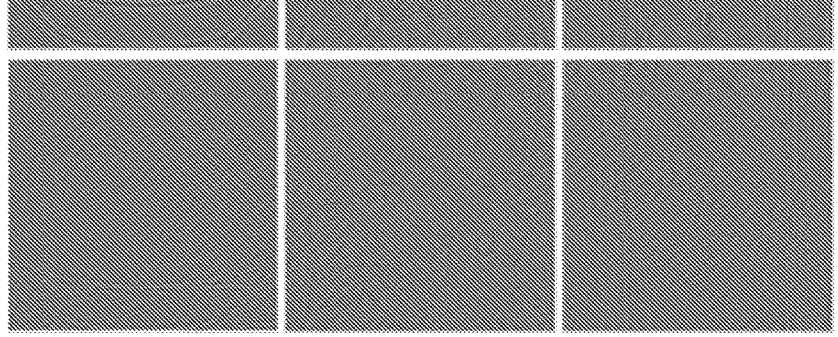

To evaluate the robustness of the ASRS approach, the process of generating perturbation patterns was repeated 100 times for each parameter point (i.e., NSD/SS and PAR). FIG. 12 shows the MSEs of the reconstructed images as a function of NSD/SS (namely, 20~200%) for four PAR cases, namely between 0 to 90%. A larger magnitude of perturbation and more frequent perturbation lead to a larger MSE in the reconstructed image. These results indicate that if the frequency of perturbation is lower than 10%, or equivalently PAR=90%, the image is robust even with up to a 200% deviation in shift size (NSD/SS=200%).

Small-Step FPS Method for ASRS

The small-step FFS approach has been tested using three different configurations: i) Full data reconstruction ([# of detector channel, # of detector row, # of angular sampling] =672×64×18444), ii) ASRS reconstruction with detector elements three times bigger (226×64×18444) than the original detector size, and iii) ASRS with sparse view reconstruction, which uses detector elements three times bigger and angular views which are 50% of the original scan of original scan (226×64×9222). In terms of data size, this data set is 16.67% of original data size.

The 3D images were reconstructed for all the cases with identical reconstruction parameters, namely dx=dy=0.75 mm and dz=0.625 mm. The axial, coronal, and sagittal plane images of 3D volume data (667×667×471) are compared in FIG. 13. Specifically, FIGS. 13 (a), (b), and (c) show reconstructed images using the same contrast window [−500, 500] HU, for the full data reconstruction, the ASRS reconstruction, and ASRS with sparse view reconstruction, respectively. The difference maps between FIGS. 13 (a) and (b) is shown in FIG. 13 (d) while the difference map between FIGS. 13 (b) and (c) is shown in FIG. 13 (e).

Thus, the present invention provides for systems and methods directed to ultra-high resolution tomographic imaging. Specifically, new system configurations are provided, along with an iterative image reconstruction that models fractional shifts of any detector elements and/or X-ray focal spot motion encoding. As such non-uniform tomographic sampling based on sub-detector ray path shifts allows for enhanced reconstruction resolution, much greater than what conventional arguments would predict based on detector size.

Fractional shifts of system detectors were described using a mathematical approach based on a modified Archimedean Spiral on Radon Space. Alternatively, effects similar to detector system shifting may be realized using a source shift by way of a small-step FFS. To show the efficacy and resolution recovery of azimuthal under-sampling and the additionally angular under-sampling, 2D and 3D tomographic simulation examples were presented. As shown, the approach of the present invention may implemented on current tomographic systems, for example, such as helical cone-beam systems with multi-row detector configurations, whereby modifying a flying focal spot motion instead of a detector motion facilitates view-by-view deflections of the focal spot.

The approach of the present invention may make it possible to reduce the complexity and cost of next generation tomographic systems while keeping a desired system resolution. This may be achieved by replacing smaller, more expensive photocounting detector elements, which may additionally necessitate dense and more complex data acquisition systems, with larger, cheaper detector elements. Also, the present invention provides for the ability to use inhomogeneous detector sets (for example, interleaved) for use in, for example, spectral imaging without losing resolution. As such, next generation systems may be developed with improved axial resolution, Z-slice sensitivity, and so on, at reduced cost.

In addition, the present invention may also provide enhanced performance of any current tomographic systems, as described. In some aspects, such systems are designed for applications that are less sensitive to resolution and use larger detector elements, for example attenuation correction in PET/CT systems. Also, such systems may utilize double armed spiral patterns for dual detector/source systems, for example dual Source CT, dual head SPECT gamma camera and so on. Other envisioned configurations include a combination of the approach of present invention with any features or aspects associated with other image improvement strategies, such as gantry wobbling, gantry rotation or table motion, to achieve a super-resolution, for example, in CT or PET systems.

Figure 14A:
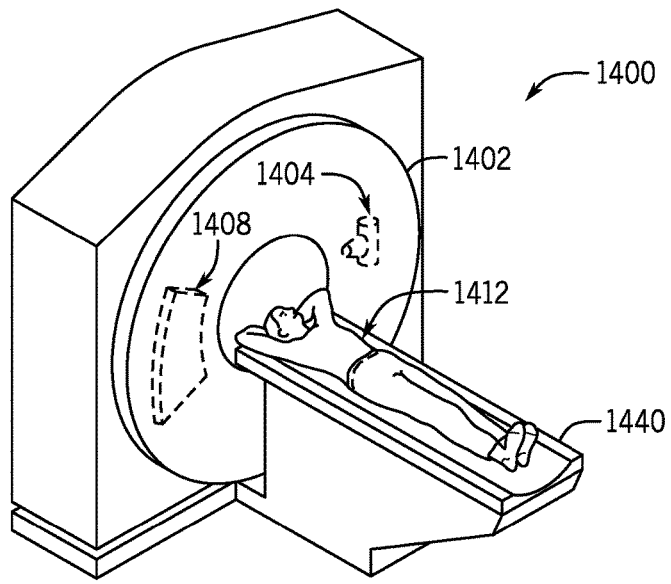
FIG. 14A is a perspective view of an example of an x-ray computed tomography ("CT") system that may implement some embodiments of the present invention.
Figure 14B:
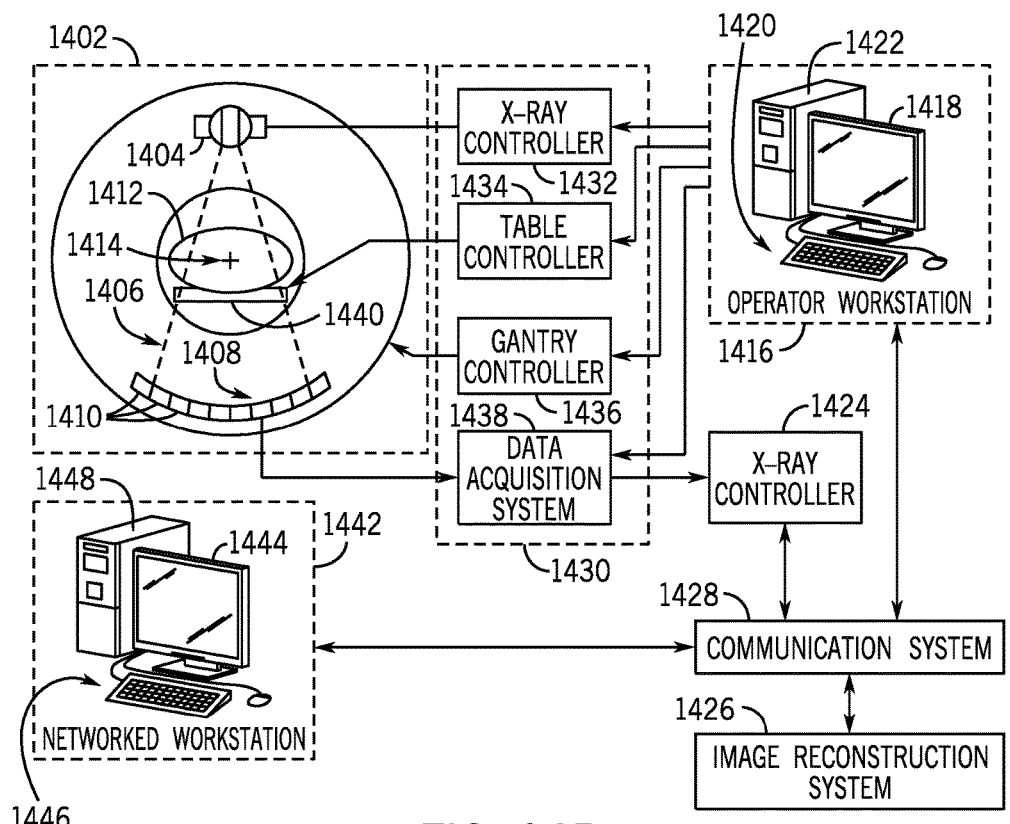
FIG. 14B, is a block diagram of an example of an x-ray CT system that may implement some embodiments of the present invention.

Referring particularly now to FIGS. 14A and 14B, an example of an x-ray computed tomography ("CT") imaging system 1400 is illustrated. The CT system includes a gantry 1402, to which at least one x-ray source 1404 is coupled. The x-ray source 1404 projects an x-ray beam 1406, which may be a fan-beam or cone-beam of x-rays towards a detector array 1408 on the opposite side of the gantry 1402. The detector array 1408 includes a number of x-ray detector elements 1410. Together, the x-ray detector elements 1410 sense the projected x-rays 1406 that pass through a subject 1412, such as a medical patient or an object undergoing examination, that is positioned in the CT system 1400. Each x-ray detector element 1410 produces an electrical signal that may represent the intensity of an impinging x-ray beam and, hence, the attenuation of the beam as it passes through the subject 1412. In some configurations, each x-ray detector 1410 is capable of counting the number of x-ray photons that impinge upon the detector 1410. During a scan to acquire x-ray projection data, the gantry 1402 and the components mounted thereon rotate about a center of rotation 1414 located within the CT system 1400.

The CT system 1400 also includes an operator workstation 1416, which typically includes a display 1418; one or more input devices 1420, such as a keyboard and mouse; and a computer processor 1422. The computer processor 1422 may include a commercially available programmable machine running a commercially available operating system. The operator workstation 1416 provides the operator interface that enables scanning control parameters to be entered into the CT system 1400. In general, the operator workstation 1416 is in communication with a data store server 1424 and an image reconstruction system 1426. By way of example, the operator workstation 1416, data store sever 1424, and image reconstruction system 1426 may be connected via a communication system 1428, which may include any suitable network connection, whether wired, wireless, or a combination of both. As an example, the communication system 1428 may include both proprietary or dedicated networks, as well as open networks, such as the internet.

The operator workstation 1416 is also in communication with a control system 1430 that controls operation of the CT system 1400. The control system 1430 generally includes an x-ray controller 1432, a table controller 1434, a gantry controller 1436, and a data acquisition system 1438. The x-ray controller 1432 provides power and timing signals to the x-ray source 1404 and the gantry controller 1436 controls the rotational speed and position of the gantry 1402. The table controller 1434 controls a table 1440 to position the subject 1412 in the gantry 1402 of the CT system 1400.

In some embodiments of the invention, the control system 1430 can control the shifts applied to the x-ray detector 1408, the x-ray source 1404, or both. For instance, the x-ray controller 1432 can be adapted to control mechanical shifting of the x-ray source 1404 or electromagnetic steering of the x-ray beam 1406, thereby effectively shifting the x-ray source 1404 position relative to the x-ray detector 1408. In other embodiments, the control system 1430 can be configured to apply shifts to the x-ray detector 1408 as that gantry 1402 is rotated about the subject 1412.

The DAS 1438 samples data from the detector elements 1410 and converts the data to digital signals for subsequent processing. For instance, digitized x-ray data is communicated from the DAS 1438 to the data store server 1424. The image reconstruction system 1426 then retrieves the x-ray data from the data store server 1424 and reconstructs an image therefrom. The image reconstruction system 1426 may include a commercially available computer processor, or may be a highly parallel computer architecture, such as a system that includes multiple-core processors and massively parallel, high-density computing devices. Optionally, image reconstruction can also be performed on the processor 1422 in the operator workstation 1416. Reconstructed images can then be communicated back to the data store server 1424 for storage or to the operator workstation 1416 to be displayed to the operator or clinician.

The CT system 1400 may also include one or more networked workstations 1442. By way of example, a networked workstation 1442 may include a display 1444; one or more input devices 1446, such as a keyboard and mouse; and a processor 1448. The networked workstation 1442 may be located within the same facility as the operator workstation 1416, or in a different facility, such as a different healthcare institution or clinic.

The networked workstation 1442, whether within the same facility or in a different facility as the operator workstation 1416, may gain remote access to the data store server 1424 and/or the image reconstruction system 1426 via the communication system 1428. Accordingly, multiple networked workstations 1442 may have access to the data store server 1424 and/or image reconstruction system 1426. In this manner, x-ray data, reconstructed images, or other data may exchanged between the data store server 1424, the image reconstruction system 1426, and the networked workstations 1442, such that the data or images may be remotely processed by a networked workstation 1442. This data may be exchanged in any suitable format, such as in accordance with the transmission control protocol ("TCP"), the internet protocol ("IP"), or other known or suitable protocols.

Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A method for producing an image of a subject with a tomographic imaging system, the steps of the method comprising:

directing a tomographic imaging system to rotate a radiation detector through a plurality of angular positions around a subject;

acquiring data with the tomographic imaging system by directing the tomographic imaging system to shift the radiation detector by a different shift value at each angular position; and reconstructing an image of the subject from the acquired data.

2. The method as recited in claim 1, wherein the shift value is a fractional shift value that is a fraction of a size of the radiation detector.

3. The method as recited in claim 2, wherein the fraction of the size of the radiation detector is 1/n for the nth angular position through which the radiation detector is rotated.

4. The method as recited in claim 1, wherein the radiation detector is shifted by the different shift value at each angular position such that the radiation detector is moved to create a spiral sampling pattern on a polar coordinate Radon space.

5. The method as recited in claim 4, wherein the spiral sampling pattern includes an Archimedean spiral on the polar coordinate Radon space.

6. The method as recited in claim 1, wherein reconstructing the image of the subject includes minimizing an energy functional that accounts for the different shift values applied to the radiation detector.

7. A tomographic imaging system comprising:
a gantry configured to rotate about a rotation axis;
a detector system coupled to the gantry and configured to detect radiation incident on the detector system;
a controller configured to:
direct the gantry to rotate the detector system through a plurality of different angular positions; and
shift the detector system by a different shift value at each of the plurality of different angular positions.

8. The tomographic imaging system as recited in claim 7, wherein the controller is configured to shift the detector system by a fractional shift value at each different angular position.

9. The tomographic imaging system as recited in claim 8, wherein the fractional shift value is computed as a fraction of a size of a detector element in the detector system.

10. The tomographic imaging system as recited in claim 7, wherein the controller is configured to shift the detector system such that the detector system is moved through a trajectory that defines a spiral sampling pattern on a polar coordinate Radon space.

11. The tomographic imaging system as recited in claim 10, wherein the spiral sampling pattern includes an Archimedean spiral.

12. A method for producing an image of a subject with a tomographic imaging system, the steps of the method comprising:
directing a tomographic imaging system to rotate a radiation detector through a plurality of angular positions around a subject;
directing the tomographic imaging system to shift a radiation source relative to the radiation detector by a different shift value at each of the plurality of angular positions;
acquiring data with the tomographic imaging system at each angular position; and
reconstructing an image of the subject from the acquired data.

13. The method as recited in claim 12, wherein directing the tomographic imaging system to shift the radiation source includes directing the tomographic imaging system to mechanically shift the radiation source.

14. The method as recited in claim 12, wherein directing the tomographic imaging system to shift the radiation source includes directing the tomographic imaging system to electromagnetically steer a radiation beam generated by the radiation source such that the radiation beam incident on the radiation source is shifted by the respective shift value.

15. The method as recited in claim 12, wherein the shift value is a fractional shift value that is a fraction of a size of the radiation detector.

16. The method as recited in claim 15, wherein the fraction of the size of the radiation detector is 1/n for the nth angular position through which the radiation source is rotated.

17. The method as recited in claim 12, wherein the radiation source is shifted by the different shift value at each angular position such that the radiation source is moved to create a spiral sampling pattern on a polar coordinate Radon space.

18. The method as recited in claim 17, wherein the spiral sampling pattern includes an Archimedean spiral on the polar coordinate Radon space.

19. The method as recited in claim 12, wherein reconstructing the image of the subject includes minimizing an energy functional that accounts for the different shift values applied to the radiation source.

* * * * *

UNITED STATES PATENT AND TRADEMARK OFFICE
CERTIFICATE OF CORRECTION

PATENT NO. : 9,629,602 B2
APPLICATION NO. : 14/758921
DATED : April 25, 2017
INVENTOR(S) : Synho Do et al.

It is certified that error appears in the above-identified patent and that said Letters Patent is hereby corrected as shown below:

In the Specification

Column 8, Line 51, "ITS" should be --FFS--.

Column 10, Line 16, "FPS" should be --FFS--.

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*